(12) United States Patent
Hinrichs et al.

(10) Patent No.: US 7,598,215 B2
(45) Date of Patent: Oct. 6, 2009

(54) HYDROXYL-CONTAINING SURFACTANTS WITH LOW SURFACE TENSION AND THEIR USE THEREOF

(75) Inventors: Petra Hinrichs, Bochum (DE); Kathrin Lehmann, Leverkusen (DE); Isabella Ulrich-Brehm, Ratingen (DE); Bernd Weyershausen, Essen (DE)

(73) Assignee: Goldschmidt GmbH, Essen (DE)

( * ) Notice: Subject to any disclaimer, the term of this patent is extended or adjusted under 35 U.S.C. 154(b) by 405 days.

(21) Appl. No.: 11/277,184

(22) Filed: Mar. 22, 2006

(65) Prior Publication Data

US 2006/0217284 A1 Sep. 28, 2006

(30) Foreign Application Priority Data

Mar. 24, 2005 (EP) .................................. 05006515

(51) Int. Cl.
*C11D 1/74* (2006.01)
*C11D 11/00* (2006.01)

(52) U.S. Cl. ..................... 510/360; 510/421; 510/475; 510/505; 510/535

(58) Field of Classification Search ................. 510/360, 510/421, 475, 505, 535
See application file for complete search history.

(56) References Cited

U.S. PATENT DOCUMENTS

| | | |
|---|---|---|
| 2,997,447 A | 8/1961 | Russell et al. |
| 6,495,727 B1 * | 12/2002 | Jordan et al. ................. 568/618 |
| 2004/0077904 A1 * | 4/2004 | Nagasawa et al. ........... 568/672 |

FOREIGN PATENT DOCUMENTS

EP 0 897 744 B1 2/1999

* cited by examiner

*Primary Examiner*—Brian P Mruk
(74) *Attorney, Agent, or Firm*—Frommer Lawrence & Haug LLP (57) ABSTRACT

The invention provides hydroxyl-containing surfactants with low surface tension and provides for their use as surfactants in aqueous coating formulations, the surfactants being preparable by reacting one or more epoxides of formula (I)

$$R^1-X-CH_2-CH-CH_2 \atop \diagdown O \diagup \quad (I)$$

with at least one hydroxy compound of formula (II)

$$HO-R^2-Y \quad (IIa)$$

$$HO-R^3-OH \atop | \atop Y \quad (IIb)$$

and/or at least one, or two or more, amine(s) of formula (III)

$$R^8 \diagdown N-R^4-Z \atop R^9 \diagup \quad (IIIa)$$

$$R^8 \diagdown N-R^5-N \diagup R^{10} \atop R^9 \diagup | \diagdown R^{11} \atop Z \quad (IIIb)$$

reacted in preferably either approximately equivalent amounts of hydroxy and/or amino groups with epoxide groups, or with an excess of hydroxy or amine hydrogen atoms, respectively.

14 Claims, 1 Drawing Sheet

Dynamic surface tension 0.5% by weight in demineralized water

FIGURE 1

HYDROXYL-CONTAINING SURFACTANTS WITH LOW SURFACE TENSION AND THEIR USE THEREOF

Any foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

The invention relates to low surface tension surfactants containing hydroxyl groups, and to their use as surfactants in aqueous coating formulations.

Water-based paints and coatings are used on a large scale industrially. Critical to effective wetting of the substrate is the lowering of the surface tension of the aqueous system by means of a surfactant. Here it is not only the lowering of the static surface tension to a small value that is decisive, but also the corresponding lowering of the dynamic surface tension. A low dynamic surface tension is needed in particular for high-speed applications, for example, when applying coatings by spraying, or in printing operations. Furthermore, the surfactants used must not disrupt the formation of a uniform film, must not cause any turbidity, and should be low-foaming—that means they should not promote the build-up of significant amounts of foam.

Water-based paints and coatings include formulations which, while being aqueous systems, include fractions of organic solvents alongside the water, such as is mandatory as a result, for example, of the use of glycols as antifreeze agents or used in the form of humectants in aqueous pigment pastes, or else as film-forming assistants or lowering the minimum film formation temperature of numerous aqueous dispersions.

Although nonionic surfactants such as alkylaryl ethoxylates or alcohol ethoxylates or ethylene oxide (EO)-propylene oxide (PO) copolymers are certainly capable of reducing the static surface tension, the high molecular weight and resultant low molecular mobility of these classes of compounds mean that it is not possible to lower the dynamic surface tension to a value which is acceptable to the user.

Conversely, some anionic surfactants, such as the sodium salts of monoalkyl or dialkyl sulfosuccinates, are able effectively to reduce the dynamic surface tension, but using them leads to severe build-up of foam in application, and the finished coating reacts sensitively to water.

More recently a new class of surfactants has been developed, based on acetylenic glycols and their alkoxylates. The properties of these surfactants are situated between those of the surfactants outlined above. With these new surfactants it is possible to reduce both the static and the dynamic surface tension, although the values which can be achieved do not entirely match those of the aforementioned nonionic and anionic groups of surfactants. On the plus side, these surfactants provide comparatively low-foam formulations (EP-B-0 897 744, U.S. Pat. No. 2,997,447).

In view of these properties, surfactants of this kind have been able to establish themselves convincingly in numerous applications. Their properties are attributed primarily to the rigid acetylenic alkyl spacer, which, as a result of the restricted degrees of freedom, imposes a kind of preorientation of polar and non polar groups. Responsibility for these properties is additionally ascribed to the small distance between the polar groups and to the low molecular weight (<300 g/mol), which allows the surfactant molecules to be highly mobile.

A problem with compounds of this type is that, in applications, foam build-up reoccurs after a very short time. For the user, however, it is very important to prevent this new foam build-up for as long as possible. The alternative would be to add defoamers, whose possible consequences include unwanted defects in the formation of the coating film, and problems with interlayer adhesion.

Furthermore, the ecotoxicological evaluation of products based on 2,4,6,8-tetramethyl-5-decynediol is not unproblematic, and in addition the products are labeled at least with "Xi" (irritant). From this class of substance, either only solid products are available to the coatings manufacturer, or for ease of handling the substance is made available as a 50% strength solution in various solvents, such as ethylene glycol (classed "Xn (harmful) suspected of having reproductive effects). Although alkoxylates of these substances are likewise effective, their foam prevention potential is significantly lower.

Products which find application as surfactants in low-viscosity aqueous or solvent-borne paints, inks, and other coating materials ought preferably to be neat liquids.

It is therefore clearly apparent that there has to date been no structural solution to the need for environmentally friendly surfactants, able to enjoy a positive ecotoxicological evaluation, specifically for aqueous coating systems in terms of foam prevention and foam inhibition. Although individual properties can be optimized, such optimization is generally at the expense of the other required parameters.

There is therefore a need to improve the overall profile of properties and to provide compounds which not only allow effective reduction in static and dynamic surface tension but also prevent foam build-up/new foam build-up effectively for a long time.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

In an effort to overcome the disadvantages of the prior art and to provide compounds which significantly reduce both static and dynamic surface tension and at the same time effectively inhibit the (re)formation of the foam for longer times than previously known compounds, it has now surprisingly been found that this objective can be achieved by means of specific hydroxyl-containing surfactants preparable by reacting glycidyl compounds either with alcohols or with amines containing at least one amine hydrogen.

The invention accordingly first provides hydroxyl-containing surfactants obtained by reacting one or more epoxides of formula (I)

(I)

in which

R¹ is a branched or unbranched, aromatic or nonaromatic, saturated or unsaturated residue with or without heteroatom substituents and containing 1 to 30, preferably 2 to 20, more preferably 3 to 12 carbon atoms and X is an oxygen or a carboxyl group with at least one hydroxy compound of formula (II)

where

Y is either OH or $NR^8R^9$, in which

R⁸ and R⁹ independently of one another can be H or branched or unbranched alkyl residues optionally containing one or more hydroxyl groups, preferably $C_{1-18}$ alkyl, more preferably $C_{1-10}$ alkyl, especially preferably $C_{1-5}$ alkyl;

or R⁸ and R⁹ may together form a substituted or unsubstituted 5- or 6-membered ring with or without heteroatoms, or Y is a branched or unbranched, saturated or unsaturated hydrocarbon residue with or without heteroatom substituents, preferably $C_{1-18}$ alkyl, more preferably $C_{-1-10}$ alkyl, especially preferably $C_{1-5}$ alkyl;

with the proviso that in formula (II a) there are on average ≧1, preferably ≧1.5, and in formula (II b) ≧2 epoxy-reactive hydrogen atoms in the molecule, R² and R³ independently of one another are branched or unbranched, aromatic or nonaromatic residues with or without heteroatom substituents, with or without one or more double and/or triple bonds, with or without (poly)oxyalkylene units, preferably oxyethylene and oxypropylene units, and containing 1 to 30, preferably 2 to 20, carbon atoms, more preferably 3 to 16 carbon atoms.

The invention further provides hydroxyl-containing surfactants obtained by reacting one or more epoxides of formula (I) above with at least one, or two or more, amine(s) of formula (III)

where

R⁸, R⁹, R¹⁰, and R¹¹ independently of one another can be H or unbranched or branched alkyl residues optionally containing one or more hydroxyl groups, preferably $C_{1-18}$ alkyl, more preferably $C_{1-10}$ alkyl, especially preferably $C_{1-5}$ alkyl;

or R⁸ and R⁹ together, or R¹⁰ and R¹¹ together, may form an unsubstituted or substituted 5- or 6-membered ring with or without heteroatoms, Z independently at each occurrence is either H or a secondary or tertiary amino group or another, unbranched or branched, unsaturated or saturated hydrocarbon residue with or without heteroatom substituents, preferably $C_{1-30}$ alkyl, more preferably $C_{1-20}$ alkyl, especially preferably $C_{1-5}$ alkyl;

with the proviso that in formula (III a) there are on average ≧1, preferably ≧1.5, and in formula (III b) ≧2 epoxy-reactive hydrogen atoms in the molecule, and R⁴ and R⁵ independently of one another are a branched or unbranched, saturated or unsaturated, aromatic or nonaromatic residue with or without heteroatom substituents, with or without (poly)oxyalkylene units, preferably oxyethylene and oxypropylene units, with or without —NH— groups, and containing 1 to 30, preferably 2 to 20, carbon atoms, more preferably 3 to 8 carbon atoms.

The invention further provides ether alcohols of the general formulae (IV) and (V)

in which

X is an oxygen or a carboxyl group,

R¹ is an unbranched or branched, aromatic or nonaromatic, unsaturated or saturated residue with or without heteroatom substituents and containing 1 to 30, preferably 2 to 20, more preferably 3 to 9 carbon atoms,

R² and R³ independently of one another are an unbranched or branched, aromatic or nonaromatic residue with or without heteroatom substituents, with or without one or more double and/or triple bonds, with or without (poly)oxyalkylene units, preferably oxyethylene and oxypropylene units, and containing 1 to 30, preferably 2 to 20, carbon atoms, more preferably 3 to 16 carbon atoms, R⁶ are any residues from the group of unbranched or branched, unsaturated or saturated $C_{2-30}$, preferably $C_{2-18}$, alkyl-residues with or without heteroatom substituents, m is 1 to 2, preferably >1.5 to 2, and in particular approximately 2, and n is 2 to 3, preferably >2.5 to 3 and in particular approximately 3.

The invention further provides amino alcohols of the general formulae (VI) and (VII)

(VI)

(VII)

in which

X is an oxygen or a carboxyl group, $R^1$ is an unbranched or branched, aromatic or nonaromatic, unsaturated or saturated residue with or without heteroatom substituents and containing 1 to 30, preferably 2 to 20, more preferably 3 to 9 carbon atoms, $R^4$ and $R^5$ independently of one another are an unbranched or branched, unsaturated or saturated aromatic or nonaromatic residue with or without heteroatom substituents, with or without (poly)oxyalkylene units, preferably oxyethylene and oxypropylene units, and containing 1 to 30, preferably 2 to 20, carbon atoms, more preferably 3 to 8 carbon atoms, $R^7$ are any residues from the group of unbranched or branched, unsaturated or saturated $C_{2-30}$, preferably $C_{2-18}$, alkyl-residues with or without heteroatom substituents, o is 1 or 2, p is 1 to 2, preferably >1.5 to 2, and in particular approximately 2, q is either 0 or corresponds to the number of —NH— groups in $R^4$ from formula (VI), r is 1 or 2, s is 2 to 3, preferably >2.5 to 3 and in particular approximately 3, t is either 0 or corresponds to the number of —NH— groups in $R^5$ from formula (VII).

The invention further provides for the use of the amino alcohols and/or ether alcohols of the invention as additives in aqueous formulations for, in particular, surface coatings, paints, printing inks or varnishes.

The invention further provides aqueous formulations comprising at least one of the amino alcohols and/or ether alcohols of the invention, such wetting agents being used normally in amounts from about 0.05% to about 5% by weight, preferably from about 0.1% to about 3% by weight.

The alcohols, amines, amino alcohols, and glycidyl ethers/esters used in accordance with the invention are industrial products which can be employed in the form of their respective commercially customary specifications, although in specialty applications of the amino alcohols and/or ether alcohols of the invention higher levels of purity may be required.

Particularly preferred residues $R^1$ in the epoxide are linear or branched aliphatic, cycloaliphatic, aromatic or aromatic-aliphatic residues having 3 to 12 carbon atoms.

Glycidyl ethers used include but are not limited to 2,3-epoxypropyl phenyl ether, 2,3-epoxypropyl isobutyl ether, 2,3-epoxypropyl 2'-ethylhexyl ether, 2,3-epoxypropyl 4'-tert-butyl phenyl ether, and the glycidyl ethers of various branched, primary alcohols such as Isofol® 10, Isofol® 12, Isofol® 16 and Isofol® 20 (Guerbet Alcohols from Sasol).

Glycidyl esters used include but are not limited to glycidyl neodecanoate, glycidyl 2-ethylhexanoate, and the glycidyl esters of various other aliphatic branched or unbranched carboxylic acids, such as Isocarb® 10, Isocarb® 12, Isocarb® 16, and Isocarb® 20 (Sasol Guerbet Alcohols oxidized to carboxylic acids).

Alcohols used include but are not limited to 1,4-butanediol, 1,4-butynediol, 1,4-butynediol ethoxylates and propoxylates (1 to 5 EO and/or PO/OH), 2,4,6,8-tetramethyl-5-decynediol and its ethoxylation products, isononanol and its ethoxylation/propoxylation products, glycerol, 1,2,6-hexanetriol, and polyalkylene glycols, such as polyethylene glycol, polypropylene glycol, polybutylene glycol, and other polyalkylene glycols which may be homopolymers or copolymers with a blockwise or random construction whose alkylene groups optionally are branched or are aromatic residues and whose average molecular weight is up to 1500 g/mol, more preferably between 200 and 1000 g/mol.

Amines used include but are not limited to 1,6-hexamethylediamine, 3,3,5-(3,5,5)-trimethyl-1,6-hexamethylenediamine, the homologous series of the polyalkylene polyamines such as, for example, diethylenetriamine, triethylenetetraamine, and dipropylenetriamine, etc, and various polyoxyalkyleneamines (e.g., available from BASF or as Jeffamines® from Huntsman) having 1 to 3 amino functions.

Amino alcohols used include but are not limited to 6-amino-1-hexanol, ethanolamine, diethanolamine, triethanolamine, methyldiethanolamine, ethyldiethanolamine, dimethylethanolamine, diethylethanolamine, diisopropanolamine, and 2-dibutylaminoethanol.

The ether alcohols and amino alcohols claimed are prepared using glycidyl compounds and alcohols or amines, respectively, either, preferably, in amounts which are approximately equivalent, based on epoxide groups and reactive hydroxy or amine hydrogen atoms, or with an excess of hydroxy or amine hydrogen atoms. The basis for calculation that is used is that of the OH number, amine number, and epoxide value, which are figures familiar to the skilled worker.

BRIEF DESCRIPTION OF THE DRAWINGS

The following detailed description, given by way of example, but not intended to limit the invention solely to the specific embodiments described, may best be understood in conjunction with the accompanying drawings, in which.

Figure 1:
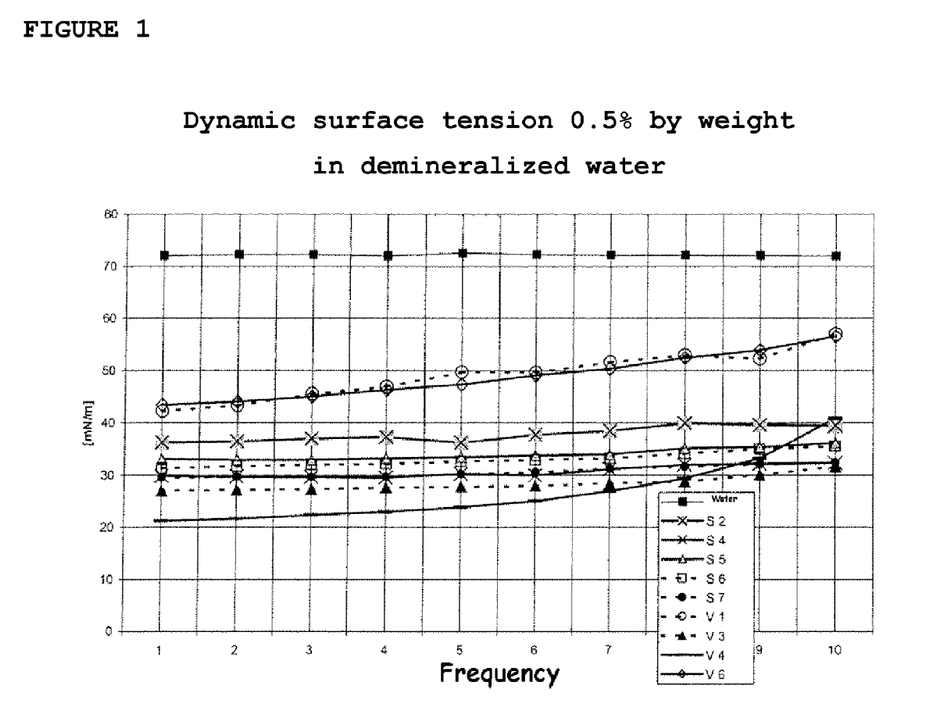
FIG. 1 depicts a comparison of the dynamic surface tension of the surfactants of the invention against non-inventive surfactants.

The invention will now be further described by way of the following non-limiting examples.

EXPERIMENTAL SECTION

Complete conversion in all reactions was verified by $^1$H NMR measurements.

Example 1

Reaction of glycidyl neodecanoate with isononanol, Etherified with ethylene oxide and propylene oxide 59.2 g (0.13 mol) of EO- and PO-etherified isononanol (OH number: 640 mg KOH/g solids) and 0.2 g (0.2% by weight) of $BF_3$-acetic acid are heated to 50° C. under nitrogen with stirring. Subsequently 30 g (0.13 mol) of glycidyl neodecanoate (epoxy value: 6.9%) are slowly added dropwise. After the end of the addition the mixture is stirred at 90° C. for 4 hours. After the end of reaction it is cooled to give a clear, pale yellow liquid.

Example 2

Reaction of glycidyl neodecanoate with ethanolamine 13.2 g (0.22 mol) of ethanolamine are heated to 50° C. under nitrogen with stirring. Subsequently 50 g (0.22 mol) of glycidyl neodecanoate (epoxy value: 6.9%) are slowly added dropwise. After the end of the addition the mixture is stirred at 90° C. for 4 hours. After the end of reaction it is cooled to give a clear, colorless liquid.

Example 3

Reaction of glycidyl neodecanoate with hexamethylenediamine 22 g (0.19 mol) of hexamethylenediamine are heated to 50° C. under nitrogen with stirring. Subsequently 90 g (0.39 mol) of glycidyl neodecanoate (epoxy value: 6.9%) are slowly added dropwise. After the end of the addition the mixture is stirred at 90° C. for 3 hours. After the end of reaction it is cooled to give a clear, light brown liquid.

Example 4

Reaction of glycidyl neodecanoate with Jeffamine® D 230(Amine-terminated Polyoxypropylene Glycol, Average Molar Mass 230 g/mol; Huntsman)

27.6 g (0.12 mol) of Jeffamine® D 230 are heated to 50° C. under nitrogen with stirring. Subsequently 55.5 g (0.24 mol) of glycidyl neodecanoate (epoxy value: 6.9%) are slowly added dropwise. After the end of the addition the mixture is stirred at 90° C. for 4 hours. After the end of reaction it is cooled to give a clear, pale yellow liquid.

Example 5

Reaction of glycidyl neodecanoate with 1,2,6-hexanetriol 15 g (0.11 mol) of 1,2,6-hexanetriol and 0.19 g (0.2% by weight) of $BF_3$-acetic acid are heated to 50° C. under nitrogen with stirring. Subsequently 77.5 g (0.33 mol) of glycidyl neodecanoate (epoxy value: 6.9%) are slowly added dropwise. After the end of the addition the mixture is stirred at 90° C. for 3 hours. After the end of reaction it is cooled to give a clear, pale yellow liquid.

Example 6

Reaction of glycidyl neodecanoate with butynediol, etherified with ethylene oxide 30.1 g (0.17 mol) of EO-etherified butynediol (OH number: 640 mg KOH/g solids) are heated to 50° C. under nitrogen with stirring. Subsequently 0.22 g (0.2% by weight) of $BF_3$-acetic acid is added and 79.5 g (0.34 mol) of glycidyl neodecanoate (epoxy value: 6.9%) are slowly added dropwise. After the end of the addition the mixture is stirred at 90° C. for 2 hours. After the end of reaction it is cooled to give a clear, light brown liquid.

Example 7

Reaction of 2,3-epoxypropyl isobutyl ether with butynediol, Etherified with ethylene oxide 40 g (0.23 mol) of EO-etherified butynediol (OH number: 640 mg KOH/g solids) and 0.2 g (0.2% by weight) of $BF_3$-acetic acid are heated to 50° C. under nitrogen with stirring. Subsequently 59.4 g (0.46 mol) of 2,3-epoxypropyl isobutyl ether are slowly added dropwise. After the end of the addition the mixture is stirred at 90° C. for 3.5 hours. After the end of reaction it is cooled to give a clear, pale yellow liquid.

Example 8

Reaction of 2,3-epoxypropyl phenyl ether with butynediol, Etherified with ethylene oxide 40 g (0.23 mol) of EO-etherified butynediol (OH number: 640 mg KOH/g solids) are heated to 50° C. under nitrogen with stirring. Subsequently 0.22 g (0.2% by weight) of $BF_3$-acetic acid is added and 68.5 g (0.46 mol) of 2,3-epoxypropyl phenyl ether are slowly added dropwise. After the end of the addition the mixture is stirred at 90° C. for 1.5 hours. After the end of reaction it is cooled to give a clear, light brown liquid.

Example 9

Reaction of glycidyl neodecanoate with dimethylaminoethanol 19.2 g (0.22 mol) of dimethylaminoethanol are heated to 50° C. under nitrogen with stirring. Subsequently 0.14 g (0.2% by weight) of $BF_3$-acetic acid is added and 50 g (0.22 mol) of glycidyl neodecanoate are slowly added dropwise. After the end of the addition the mixture is stirred at 90° C. for 4.5 hours. After the end of reaction it is cooled to give a clear, colorless liquid.

Example 10

Reaction of glycidyl neodecanoate with butynediol, Etherified with ethylene oxide 30 g (0.17 mol) of EO-etherified butynediol (OH number: 640 mg KOH/g solids) are heated to 50° C. under nitrogen with stirring. Subsequently 0.12 g (0.2% by weight) of $BF_3$-acetic acid is added and 31.2 g (0.17 mol) of glycidyl neodecanoate (epoxy value: 6.9%) are slowly added dropwise. After the end of the addition the mixture is stirred at 90° C. for 4 hours. After the end of reaction it is cooled to give a clear, pale yellow liquid.

Application Tests:

For the testing of new wetting agents a series of overview tests is performed in order to assess not only the inhibitory and/or preventative effect on foam but also the rapid, surfactant-initiated destruction of foam formed in a system by other surface-active substances. Another important criterion for grading wetting agents is their long-term effect in the sense of preventing foam even after storage of the corresponding system equipped with the wetting agent. This matter is of particular importance, since foam prevention during coating preparation is fundamentally different from foam-free application by means of spraying, knife coating or pouring, etc.; the addition of further surfactant during the application is undesirable.

Dynamic Surface Tension:

Determining the dynamic surface tension of the formulated systems is essential to be able to estimate the rate at which a wetting agent molecule reaches a newly generated interface in order to be able to make an active contribution to destroying foam.

These values are determined using the online tensiometer t 60 from SITA Messtechnik GmbH. This instrument measures the dynamic surface tension in accordance with the principle of maximum bubble pressure: the internal force of attraction of a liquid also compresses those air bubbles present in the liquid. The resultant pressure increases as the bubble radius falls. It is this pressure, increased in relation to the ambient pressure, that is utilized for the bubble pressure method. A gas stream is passed through a capillary, which is dipped in a liquid. The bubble surface which forms becomes curved and continuously reduces the radius of the bubble. The pressure increases up to a maximum value. At this value the bubble has attained its smallest radius, the capillary radius, and forms a hemisphere. When this point is exceeded the bubble bursts and tears away from the capillary, allowing a new bubble to form. This produces a characteristic pressure curve, which is evaluated in order to determine the surface tension. In other words, the smaller the value in the case of low bubble frequency, the more effective the wetting agent is in wetting a low-energy surface. The smaller the difference between the value at low bubble frequency and the value at high bubble frequency, the more capable the wetting agent is of orienting itself to newly created surfaces—that is, in being effective even during highly dynamic application processes.

The wetting agents claimed in accordance with the invention were evaluated by carrying out the tests set out in greater detail below.

Foam Inhibition Effect:

A defined amount of wetting agent is added to a defined amount of a test system and is incorporated using a toothed-wheel disk at 1 500 rpm for 1 minute. Subsequently air is introduced at 3 000 rpm for 1 minute, and foam produced. The resulting foam height is read off and viewed in comparison with the foam height reached in the absence of the wetting agent. Thereafter a measurement is made of the time taken for the foam to go down completely, something which generally does not happen at all in the absence of wetting agents.

Assessment of Foam Build-Up and of Spontaneous Defoaming:

Foam is built up in a defined amount of a test system using a perforated disk (see below) at 2 000 rpm for 1 minute. Then a defined amount of wetting agent is placed on the foam and the occurrence of spontaneous defoaming is assessed visually (bursting air bubbles, "prickling" on the surface) and graded as absent (−), present (+/−) or very characteristic (+).

Shearing with the perforated disk is then repeated at 2 000 rpm for one minute. This time a stopwatch is used to record the time which elapses before foam builds up again. If a wetting agent is able to prevent foam building up again, it is classified, with ">60 s", as very active.

A defined amount of this sample is subsequently introduced into a measuring cylinder and the foam height is recorded by reporting ml of foam and is compared with a blank sample.

The perforated disk employed actually comprises three disks arranged one above the other on a spindle (disk thickness 3 mm, disk diameter 25 mm) and each having three holes (diameter: 5 mm). The distance between the individual disks is 9 mm and they rotate vertically by 120° on the securing spindle. This apparatus allows optimum introduction of macrofoam and microfoam, such as occurs in painting application operations (such as rolling or spraying, for example) and production processes and can be prevented by suitable wetting agents.

Long-Term Effect:

Following storage of the twice-sheared sample (see test described above) for 4 to 14 days the sample is again stirred with the perforated disk at 2000 rpm for 1 minute and again the resulting foam height of the sample is read off in a measuring cylinder. Where there is hardly any difference between these values and the original determination, the wetting agent is still available in the system and hence is also found to be stable to hydrolysis.

Viscosity:

Surfactants incorporated into inks, paints and other coating materials frequently give rise to unwanted changes in the viscosity of the system, which then leads, through thickening effects, for example, to fundamentally different film thicknesses during application, and hence jeopardizes the economics. It is therefore necessary to evaluate the coating system with the surfactant added, in comparison to the unsheared blank sample without any additive. For this purpose there are a range of rheometers available, that used here being the RC 20-CPS from Europhysics. The program employed measures from 100 [1/s] to 1000 [1/s] in 180 seconds, using a cone/plate geometry.

Incompatibility:

In transparent systems even a slight turbidity points to an unwanted incompatibility of the surfactant with the surrounding matrix. To ensure that the foam preventative effect of the surfactant is not bought at the expense of turbidity imparted to clearcoats, or as a result of cratering, the skilled worker applies the corresponding coating material to different substrates for the purpose of visual evaluation (e.g., black PVC film or transparent PE film).

In the following tests the wetting agents of the invention are labeled S1 to S7.

S1 (Example 3)
S2 (Example 7)
S3 (Example 8)
S4 (Example 9)
S5 (Example 1)
S6 (Example 2)
S7 (Example 10)

Noninventive, comparative examples are the following wetting agents, which are supplied as commercial products for aqueous systems and can be characterized in accordance with the details below.

V1 2,4,7,9-tetramethyl-5-decyne-4,7-diol 100% solid surfactant
V2 2,4,7,9-tetramethyl-5-decyne-4,7-diol ethoxylate
V3 fatty alcohol alkoxylate with a molar weight of about 500 g/mol
V4 trisiloxane polyether surfactant
V5 oligo siloxane polyether surfactant
V6 styrene oxide-based block copolymer with a molar weight of about 1000 g/mol.

The aforementioned inventive and commercially customary wetting agents are deployed in the standard formulations below and the reduction in surface tension in aqueous 0.5% by weight surfactant solutions is measured.

Water-Based Printing Ink Formulation:
50 g of ink, consisting of:
JonCryl® 8085 (43% ammoniacal solution of an acrylate resin)[1] 29.4 g
JonCryl® ECO 2189 (glycol-ether-free, film-forming polymer dispersion)[1] 44.1 g
JonCryl® ECO 2177 (glycol-ether-free, film-forming polymer dispersion)[1] 17.7 g
JonWax® 35 (polyethylene wax emulsion)[1] 4.9 g demineralized water 2.9 g

[1] Johnson Polymer are weighed out into a 100 ml glass bottle, 0.5% of active matter of wetting agent is stirred in using a 2.5 cm toothed-edge disk at 1 500 rpm for 1 minute, and the mixture is then foamed at 3 000 rpm for 1 minute. The fill level (solution+foam) is read off in the glass bottle using a ruler and the time taken for the foam to collapse, in minutes, is determined using a stopwatch.

TABLE 1

Results in a water-based printing ink with prior measurement of the dynamic surface tension in water:

| Wetting agent | Foam [cm] | Dynamic surface tension of 0.5% by weight surfactant solution with 1 and 10 bubbles/sec [mN/m] |
|---|---|---|
| none | 7.0 | 72 to 72 |
| S1 | 5.5 | — |
| S2 | 5.5 | 36.2 to 39.4 |
| S3 | 5.0 | — |
| S5 | 5.0 | 33.0 to 36.1 |
| S7 | 5.5 | 29.5 to 32.4 |
| V1 | 6.0 | 42.2 to 47.0 |
| V2 | 6.0 | — |
| V3 | 6.7 | 30.2 to 32.6 |
| V4 | — | 21.2 to 40.8 |
| V6 | — | 43.4 to 56.5 |

Table 1 shows that using the wetting agents claimed in accordance with the invention significantly reduces foam build-up as compared with the blank sample and with the comparative examples. Looking, in addition, at the reduction in dynamic surface tension the surfactants claimed in accordance with the invention are able to produce in water, it becomes clear that the combination of the properties of foam reduction and availability of newly created interfaces distinguishes this innovative class of surfactant in rapid application operations such as, for example, when applying printing inks.

Furthermore, with their 100% pure liquid presentation form, they are easy to incorporate and hence user-friendly.

Accordingly, the surfactants claimed in accordance with the invention neither exhibit the unsatisfactory water solubility and resultant unsatisfactory reduction in surface tension of, for example, comparative example V1 (solid hydrophobic substance), and nor, unlike for example V4 to V6, are they limited in terms of dynamic surface tension, which particularly with 10 bubbles/sec is relevant for rapid application operations.

Water-Based Automotive Finish I:

50 g of a mixture of 2 parts of aliphatic polyurethane-acrylic hybrid dispersion Daotan® VTW 6264 (Solutia) and 1 part of DI (deionized) water in a vessel (diameter: 65 mm) are foamed at 2 000 rpm for 1 minute using a perforated disk (for description see above). 0.2% of active matter of wetting agent ingredient is placed on the resulting foam, and the spontaneous defoaming is observed. This is followed by shearing again at 2 000 rpm for 1 minute, after which the time taken for the foam to build up again is measured using a stopwatch. If the foam does not build up again, the evaluation is reported as >60 seconds.

Immediately following the shearing operation, 25 g of this sample are introduced into a 100 ml measuring cylinder, and the fill level is read off in ml.

In order to assess the stability to hydrolysis and the storage stability the sample after four days is again sheared at 2 000 rpm for 1 minute and the foam height of 25 g is determined using a 100 ml measuring cylinder.

TABLE 2

Results in an aqueous automotive finish I:

| Wetting agent | Spontaneous defoaming* | Renewed build-up of foam [sec] | Foam value instantaneous [ml/25 g] (residual foam) | Foam value after 4 days [ml/25 g] |
|---|---|---|---|---|
| blank value | n/a | n/a | 44 | 46 |
| S2 | + | 60 | 30 | 40 |
| S4 | + | 60 | 30 | 36 |
| S5 | + | 60 | 30 | 31 |
| S6 | + | 60 | 30 | 35 |
| S7 | + | >60 | 28 | 30 |
| V1 | + | 45 | 30 | 32 |
| V2 | +/− | 60 | 37 | 40 |
| V3 | + | 45 | 30 | 33 |
| V4 | − | — | 50 | 50 |
| V5 | +/− | 10 | 35 | 38 |

*(−) absent, (+/−) present, (+) very clearly marked

The compounds of the invention exhibit pronounced spontaneous defoaming. It is this property of the innovative surfactants which is of greatest interest for the coatings manufacturer. If particular products such as S4 to S7 are still selected, it is additionally possible to obtain surfactants which are also notable for particularly low residual foam values as well, and which even on further introduction of shearing are capable of long-lasting foam prevention. As a consequence it is not necessary to add additional wetting agent or defoamer to the automotive finish system, even after storage.

Very important in the positive evaluation of the compounds of the invention here is the summation of the important properties in one structure:

Spontaneous defoaming
+ renewed build-up of foam absent or very late
+ optimum reduction of foam (instantaneous + after storage)

Water-Based Automotive Finish II:

0.5% surfactant is weighed out into 10 g of a water-dilutable, self-crosslinking alkyd resin containing urethane groups, Resydrol VAZ 5541 (Solutia), and the surfactant is incorporated by stirring with a Hausschild Speedmixer at 3600 rpm for one minute.

After three days the viscosity of the samples is determined in mPas using an RC 20-CPS viscometer from Europhysics at 500 revolutions/second.

In addition the coating material is drawn down onto aluminum at 50 μm using a box-type applicator, in order to assess the compatibility.

TABLE 3

Results in an aqueous automotive finish II:

| Wetting agent | Thickening [mPas] | Characterization of coating film |
| --- | --- | --- |
| blank value | 124 | +++ |
| S2 | 123 | ++− |
| S3 | 121 | ++− |
| S5 | 127 | +++ |
| S2/S3/S5 avg. | 123.7 | 2.3+/0.7− |
| V1 | 138 | +−− |
| V2 | 132 | −−− |
| V3 | 136 | ++− |
| V5 | 129 | +−− |
| V1/V2/V3/V5 avg. | 133.8 | 1.0+/2.0− |

+++ = no defects
−−− = severe defects

Table 3, with the correspondingly low viscosities, which for the compounds claimed in accordance with the invention are at the same level as the pure automotive finish system without wetting agents (blank value), illustrates that there is virtually no increase in viscosity, in contrast to the comparative examples. Specifically in the sensitive thin-film automotive finishing applications, therefore, a solution has been found for reproducible film thickness build-up and surface image. The effective removal of air from the system, which can be demonstrated simply from the viscosities, becomes clear additionally as a result of a very good surface image of the coatings, in the form of defect-free films.

SUMMARY

The compounds claimed in accordance with the invention can be utilized without reserve as wetting agents in aqueous paints, inks, and other coating materials, since they significantly lower the surface tension, it being possible for these aqueous paints and inks to include, if desired, fractions of organic solvents.

A particularly interesting feature is that even in rapid application operations they become apparent as effective wetting agents, on account of their dynamic surface tension profile, which is virtually independent of the frequency, i.e., of the multiplicity of newly created interfaces.

The hydroxyl-containing surfactants claimed in accordance with the invention therefore combine, in a hitherto unknown profile of properties, spontaneous-defoaming properties, which are used during coatings manufacture and application, with vigorous foam destruction (residual foam values zero or very low). The last-mentioned property is found even after storage of the coating material, which implies that the compounds claimed in accordance with the invention are not subject to hydrolytic attack—that is, they are surprisingly stable. The compounds claimed in accordance with the invention do not realize foam destruction at the cost of disrupted surface image, and so even sensitive automotive finish surfaces can be applied without defect.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A hydroxyl-containing surfactant compound obtained by reacting one or more epoxides of formula (I)

in which
R$^1$ is a branched or unbranched, aromatic or nonaromatic, saturated or unsaturated residue with or without heteroatom substituents and containing 1 to 30 carbon atoms and
X is a carboxyl group
with at least one hydroxy compound of formula (II)

where
Y is either OH or NR$^8$R$^9$, in which
R$^8$ and R$^9$ independently of one another can be H or branched or unbranched alkyl residues optionally containing one or more hydroxyl groups,
or R$^8$ and R$^9$ may together form a substituted or unsubstituted 5- or 6-membered ring with or without heteroatoms,
or
Y is a branched or unbranched, saturated or unsaturated hydrocarbon residue with or without heteroatom substituents,
with the proviso that in formula (IIa) there are on average ≧1 and in formula (IIb) ≧2 epoxy-reactive hydrogen atoms in the molecule,
R$^2$ and R$^3$ independently of one another are branched or unbranched, aromatic or nonaromatic residues with or without heteroatom substituents, with or without one or more double and/or triple bonds, with or without (poly) oxyalkylene units, and containing 1 to 30 carbon atoms.

2. A compound as claimed in claim 1, wherein the residue R$^1$ of the epoxide is a branched saturated residue having two to twenty carbon atoms.

3. A compound as claimed in claim 1, wherein the hydroxy compound of formula (II) contains one or more double and/or triple bonds for the residues R$^2$ and R$^3$.

4. The hydroxyl-containing surfactant compound of claim 1, wherein
R$^1$ is a branched or unbranched, aromatic or nonaromatic, saturated or unsaturated residue with or without heteroatom substituents and containing 2 to 20 carbon atoms;
R$^2$ and R$^3$ independently of one another are branched or unbranched, aromatic or nonaromatic residues with or without heteroatom substituents, with or without one or more double and/or triple bonds, with or without (poly)oxyalkylene units, and containing 2 to 20 carbon atoms; and with the proviso that in formula (IIa) there are on average $\geq 1.5$, and in formula (IIb) $\geq 2$ epoxy-reactive hydrogen atoms in the molecule.

5. The hydroxyl-containing surfactant compound of claim 4, wherein
$R^1$ is a branched or unbranched, aromatic or nonaromatic, saturated or unsaturated residue with or without heteroatom substituents and containing 3 to 12 carbon atoms;
$R^2$ and $R^3$ independently of one another are branched or unbranched, aromatic or nonaromatic residues with or without heteroatom substituents, with or without one or more double and/or triple bonds, with or without (poly)oxyalkylene units, and containing 3 to 16 carbon atoms.

6. An ether alcohol of the general formulae (IV) and (V)

in which
X is a carboxyl group,
$R^1$ is an unbranched or branched, aromatic or nonaromatic, unsaturated or saturated residue with or without heteroatom substituents and containing 1 to 30,
$R^2$ and $R^3$ independently of one another are an unbranched or branched, aromatic or nonaromatic residue with or without heteroatom substituents, with or without one or more double and/or triple bonds, with or without (poly)oxyalkylene units, and containing 1 to 30,
$R^6$ are any residues from the group of unbranched or branched, unsaturated or saturated residues with or without heteroatom substituents,
m is 1 to 2, and
n is 2 to 3.

7. The ether alcohol of claim 6, wherein:
$R^1$ is an unbranched or branched, aromatic or nonaromatic, unsaturated or saturated residue with or without heteroatom substituents and containing 2 to 20 carbon atoms,
$R^2$ and $R^3$ independently of one another are an unbranched or branched, aromatic or nonaromatic residue with or without heteroatom substituents, with or without one or more double and/or triple bonds, with or without (poly)oxyalkylene units, and containing 2 to 20 carbon atoms,
m is >1.5 to 2,
n is >2.5 to 3.

8. The ether alcohol of claim 6, wherein:
$R^1$ is an unbranched or branched, aromatic or nonaromatic, unsaturated or saturated residue with or without heteroatom substituents and containing 3 to 9 carbon atoms,
$R^2$ and $R^3$ independently of one another are an unbranched or branched, aromatic or nonaromatic residue with or without heteroatom substituents, with or without one or more double and/or triple bonds, with or without (poly)oxyalkylene units, and containing 3 to 16 carbon atoms,
m is approximately 2,
n is approximately 3.

9. A method of making a low foaming aqueous formulation which comprises adding at least one compound as claimed in claim 1 to the aqueous formulation.

10. The method of claim 9, wherein the aqueous formulation is a surface coating, paint, printing ink or varnish.

11. A low-foaming aqueous formulation comprising at least one compound as claimed in claim 1 in an amount from 0.05% to 5% by weight.

12. The low-foaming aqueous formulation of claim 11, wherein the aqueous formulation is a surface coating, paint, printing ink or varnish.

13. The compound as claimed in claim 3, wherein the (poly)oxyalkylene units are oxyethylene and/or oxypropylene units.

14. The ether alcohol of claim 8, wherein the (poly)oxyalkylene units are oxyethylene and/or oxypropylene units.

* * * * *

UNITED STATES PATENT AND TRADEMARK OFFICE
CERTIFICATE OF CORRECTION

PATENT NO. : 7,598,215 B2
APPLICATION NO. : 11/277184
DATED : October 6, 2009
INVENTOR(S) : Hinrichs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Twenty-eighth Day of September, 2010

David J. Kappos
*Director of the United States Patent and Trademark Office*